(12) United States Patent
Raynor

(10) Patent No.: US 7,447,385 B2
(45) Date of Patent: Nov. 4, 2008

(54) BIO-OPTICAL SENSORS

(75) Inventor: Jeffrey Raynor, Edinburgh (GB)

(73) Assignee: STMicroelectronics Ltd., Buckinghamshire (GB)

( * ) Notice: Subject to any disclaimer, the term of this patent is extended or adjusted under 35 U.S.C. 154(b) by 865 days.

(21) Appl. No.: 11/015,242

(22) Filed: Dec. 17, 2004

(65) Prior Publication Data

US 2005/0141058 A1   Jun. 30, 2005

(30) Foreign Application Priority Data

Dec. 19, 2003   (EP)   ................................. 03258086

(51) Int. Cl.
  *G06K 7/00*   (2006.01)
  *G01N 21/59*   (2006.01)
  *H04N 1/04*   (2006.01)

(52) U.S. Cl. ........................ 382/312; 356/436

(58) Field of Classification Search ................ 382/141, 382/144, 145, 312; 356/215, 222, 317, 436, 356/440, 450; 250/239; 257/98; 422/50, 422/52, 82.08; 427/2.11; 438/29
See application file for complete search history.

(56) References Cited

U.S. PATENT DOCUMENTS

| | | | |
|---|---|---|---|
| 5,096,807 A | 3/1992 | Leaback | 435/6 |
| 5,194,393 A * | 3/1993 | Hugl et al. | 436/525 |
| 6,278,523 B1 * | 8/2001 | Gorecki | 356/450 |
| 6,542,241 B1 | 4/2003 | Thorwirth et al. | 356/436 |
| 6,646,744 B2 * | 11/2003 | Pedersen et al. | 356/445 |
| 6,649,357 B2 | 11/2003 | Bryan et al. | 435/7.1 |
| 7,273,633 B2 * | 9/2007 | Raynor | 427/2.11 |
| 7,286,210 B2 * | 10/2007 | Pettit | 356/32 |
| 2002/0115224 A1 * | 8/2002 | Rudel et al. | 436/164 |
| 2004/0227068 A1 * | 11/2004 | Raynor et al. | 250/239 |
| 2005/0141058 A1 * | 6/2005 | Raynor | 358/504 |
| 2005/0151148 A1 * | 7/2005 | Raynor | 257/98 |

FOREIGN PATENT DOCUMENTS

WO   01/36926   5/2001

OTHER PUBLICATIONS

Eggers et al., A Microchip for Quantitative Detection of Molecules Utilizing Luminescent and Radioisotope Reporter Groups, Biotechniques, Eaton Publishing, Natick, US, vol. 17, No. 3, 1994.

* cited by examiner

*Primary Examiner*—Amir Alavi
(74) *Attorney, Agent, or Firm*—Lisa K. Jorgenson; Allen, Dyer, Doppelt, Milbrath & Gilchrist, P.A.

(57) ABSTRACT

A bio-optical sensor has a surface provided with an array of sensing pixels and calibration pixels. The sensing and calibration pixels are arranged in an interleaved fashion. The sensing and calibration pixels may be interleaved 1:1, or they may be arranged in interleaved blocks. The image plane receives an analyte and a reagent that reacts with the analyte to produce light. The sensing pixels generate signals as a function of the light produced.

28 Claims, 4 Drawing Sheets

IMPROVED SENSOR CALIBRATION WITH INTERLEAVED PIXELS.

BIO-OPTICAL SENSORS

FIELD OF THE INVENTION

The present invention relates to bi-optical sensors, and in particular, to a light-sensitive semiconductor device for detecting and measuring light emitted by the reaction of a reagent with a biological sample.

BACKGROUND OF THE INVENTION

In known bio-optical sensors, the reaction takes place on a surface of the semiconductor device which is an image surface divided into pixels. The light produced by reactions of this nature is small, and accordingly, the signal produced by any pixel of the device is also small. The signal is frequently less than other effects such as dark current (leakage current) from the pixel and voltage offsets. Therefore, a calibration/cancellation scheme may be necessary to increase the sensitivity of the system.

In the related field of solid state image sensors, there are a number of known calibration techniques. In image sensors, it may be necessary to have a continuous image plane on which the image is formed. Calibration techniques involve either the use of dark frame cancellation or the use of special calibration pixels.

In dark frame cancellation, a dark reference frame is taken and the resulting signal output is subtracted from the image frame. The dark reference frame is usually taken with the same exposure. The integration time is the same as the image but no light is impinged on the sensor, either by use of a shutter or by turning off the scene illumination.

When calibration pixels are used, they are provided at the edge of the sensor. The calibration pixels are usually in the form of a single row or column, since it is necessary to have a continuous image surface.

In current bio-optical sensors, a dark image is acquired before the analyte and reagents are deposited on the sensor. This calibration image is used during detection and processing of the photo-signal. This means that there is a time difference between the acquisition of the dark reference frame and the detection and processing of the sensor signal. During this time there may be changes in the conditions on the device, e.g., operating voltage and temperature may change due to a low battery, a change in the ambient temperature, or self-heating due to power dissipation. Consequently, the calibration signal is not an accurate representation of the dark signal at the relevant time.

SUMMARY OF THE INVENTION

An object of the present invention is to provide a bio-optical sensor having a more accurate calibration signal. A more accurate calibration signal increases system sensitivity and enables the system to function with less analyte, less reagent, or in a shorter time.

Accordingly, the invention provides a bio-optical sensor comprising a semiconductor substrate having an image plane formed as an array of pixels. The image plane may receive thereon an analyte and a reagent which reacts with the analyte to produce light. The pixels may comprise sensing pixels which generate signals which are a function of light emitted by the reaction, and calibration pixels which are not exposed to the light. The calibration pixels may be interleaved with the sensing pixels.

Preferred features and other advantages of the invention will be apparent from the following description and from the claims.

BRIEF DESCRIPTION OF THE DRAWINGS

Embodiments of the invention will now be described, by way of example only, with reference to the drawings, in which.

DETAILED DESCRIPTION OF THE PREFERRED EMBODIMENTS

Figure 1:
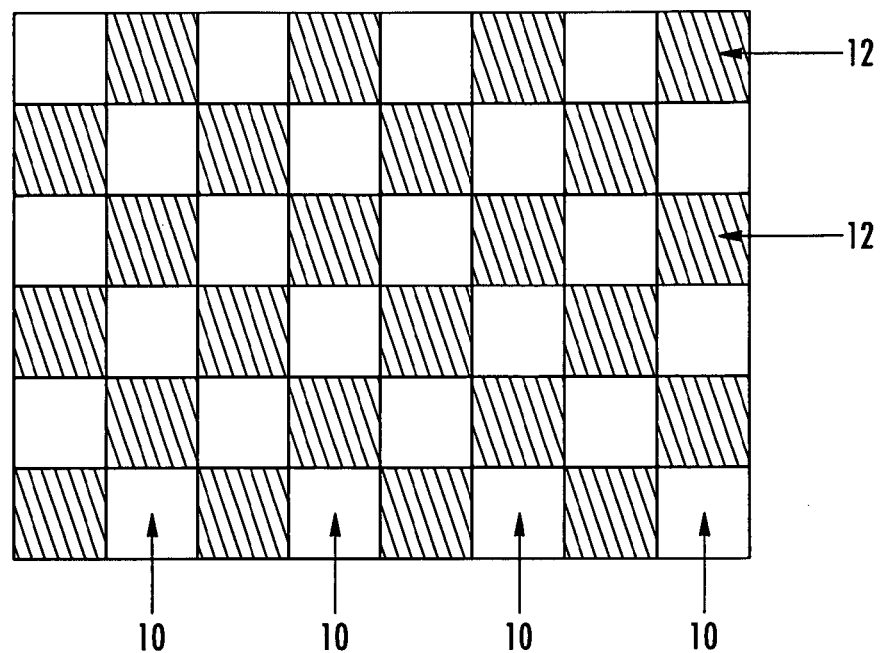
FIG. 1 is a schematic plan view of the image area in accordance with the invention.

FIG. 1 shows a straightforward form of the invention in which the image surface is divided into sensing pixels 10 and calibration pixels 12 which are interleaved on a 1:1 basis, i.e., in a checker board fashion. Each of the pixels 10, 12 is an imaging pixel of a well-known type, such as a 3-transistor or 4-transistor pixel based on CMOS technology. The calibration pixels 12 are shielded from light by a suitable mask, which may be printed on top of the array or may be formed by selective metallization during fabrication, for example. When a metal mask is used, there is preferably a layer separated from the readout electronics to reduce parasitic capacitance.

Alternatives to metallization for forming the opaque layer include silicided gate oxide, and superposition of color filters, i.e., overlaying red green and blue filters to give black.

It is preferable that the border pixels situated at the edge of the sensor are not used, either for sensing or calibration. The border pixels have neighboring pixels on less than four sides, whereas the other pixels have neighboring pixels on all four sides. Also, practical issues with the fabrication processing of the sensor cause variations in the size of the patterned features that will be exacerbated at the edges. These factors change the analog performance of the border pixels at the edges, and thus the border pixels are best ignored.

In the arrangement of FIG. 1, the entire image surface may be covered with analyte and reagent since it would be difficult to physically contain a liquid system to single pixel areas. This has the disadvantage that only 50% of the analyte and reagent is available to the sensing pixels, while the quantities of both are usually limited by problems obtaining a sample and the costs of the reagent.

This problem can be addressed by dividing the surface into sensitive regions and calibration regions. This allows the analyte and reagent to be applied only to the sensitive regions.

Figure 2:
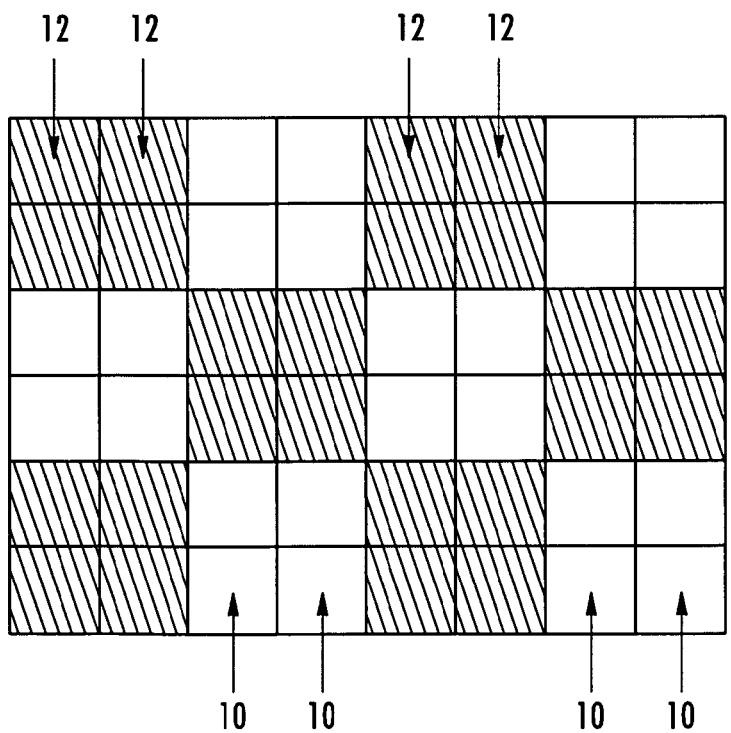
FIGS. 2, 3 and 4 are schematic plan views of further embodiments of the image area in accordance with the invention.
Figure 3:
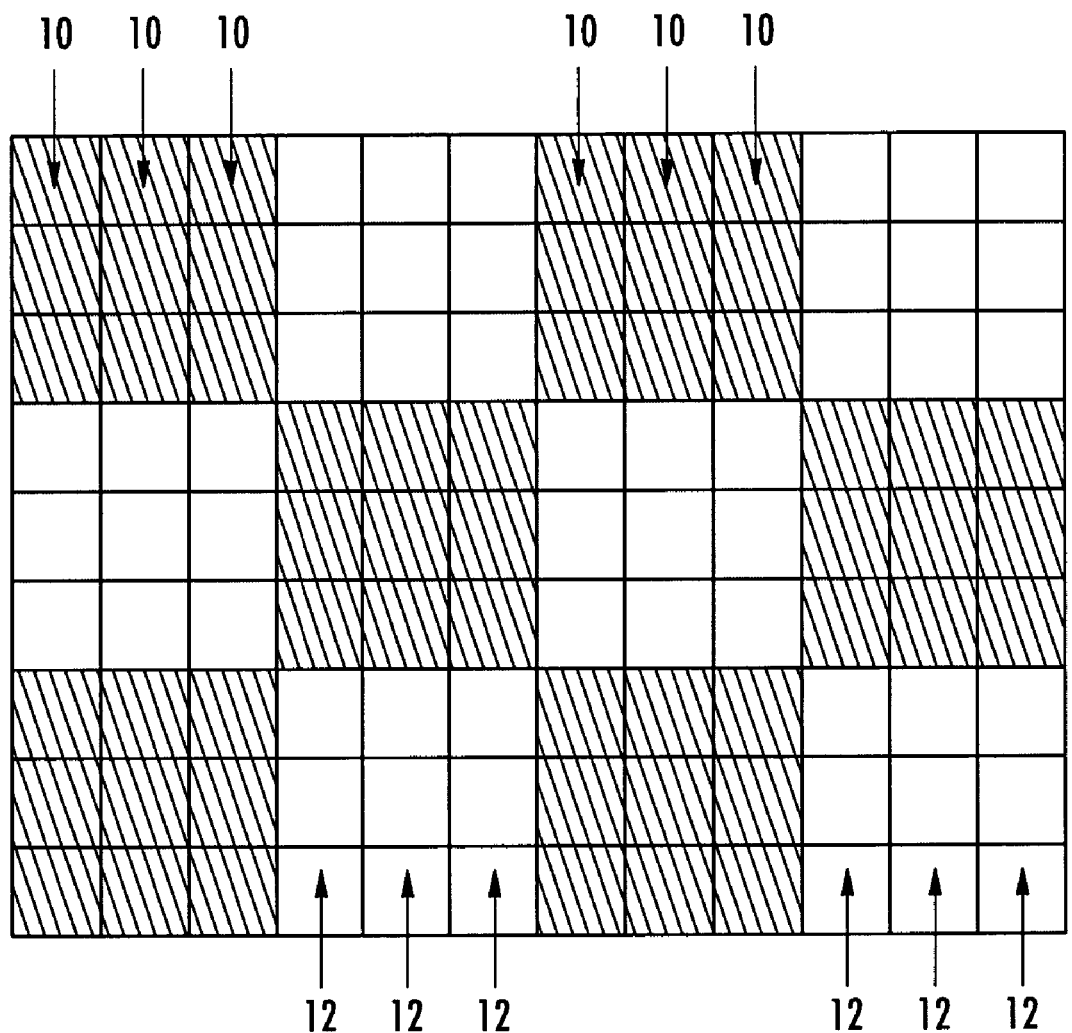
Figure 4:
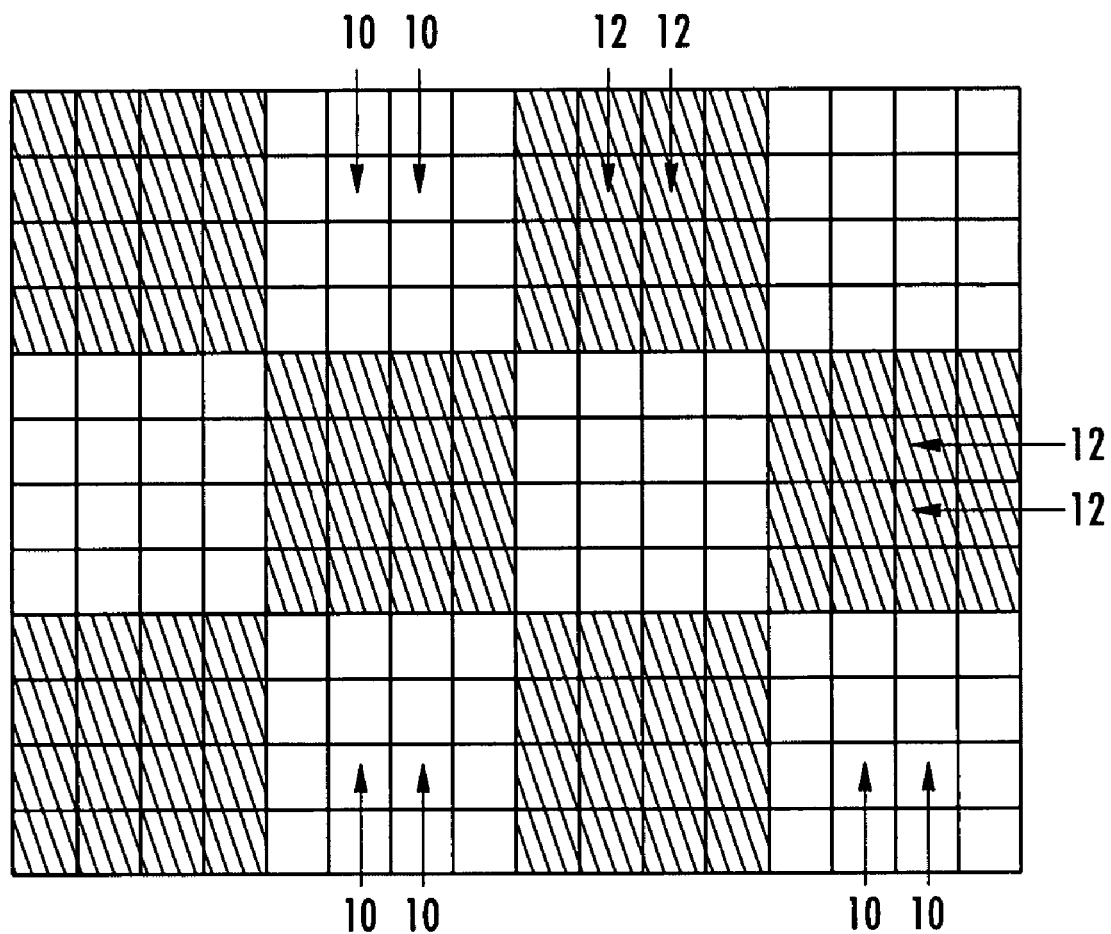

FIG. 2 shows an interleaving scheme using 2×2 blocks of pixels. However, interleaving in blocks does pose problems. It is reasonable to assume that an edge pixel of a block will have a response significantly different to interior pixels, and should be discarded. Thus, the FIG. 2 array may not be practicable. FIG. 3 shows an array interleaved in blocks of 3×3 in which, if the edge pixels are not used, only ⅑ of the surface area will be effective. FIG. 4 shows an array interleaved in 4×4 blocks in which ¼ of the area will be effective if edge pixels are not used.

Figure 5:
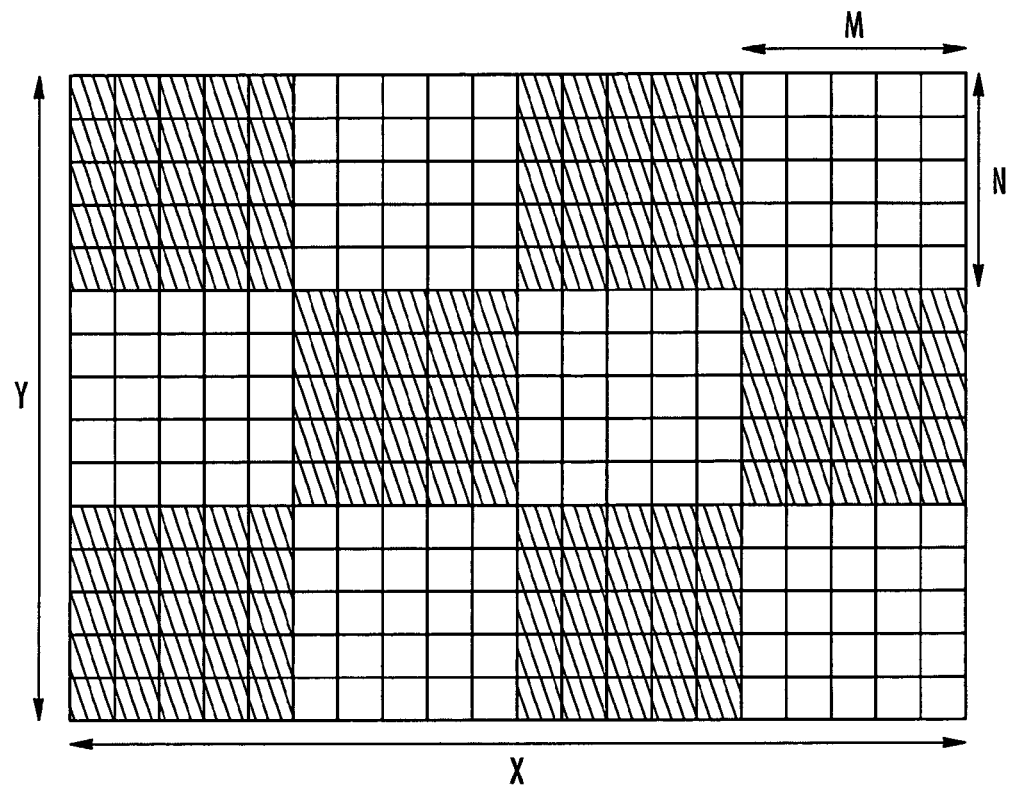
FIG. 5 illustrates a general case of the image area in accordance with the invention.

FIG. 5 shows the general case where the sensor has X (horizontal) by Y (vertical) pixels arranged in blocks of M×N pixels. Each block therefore has (M−2)×(N−2) useful pixels. The graph of FIG. 6 shows the percentage of useful pixels for different block sizes, assuming square blocks with M=N.

Figure 6:
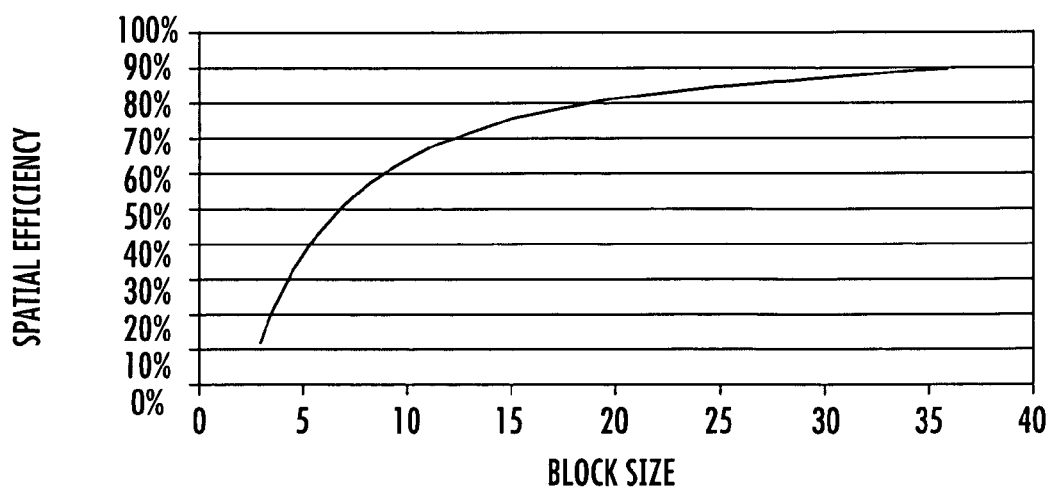
FIG. 6 is a graph showing the relationship between the size of pixel blocks and spatial efficiency in accordance with the invention.

If we define spatial efficiency=100×(No. of useful pixels/total no. of pixels), then FIG. 6 shows that with block sizes of 6×6 or less the spatial efficiency is less than 50%, i.e., worse than the straightforward 1×1 interleave form. For 7×7 blocks, spatial efficiency is greater than 50%, i.e., there is an improvement over the 1×1 form.

The graph also illustrates the point of diminishing returns. With 20×20 pixels, the efficiency is 80% and increases only slowly from this point. The most useful block size is likely to lie in the range of 20-30 pixels.

The foregoing embodiments show the blocks of sensing and calibration pixels distributed in a common-centered manner, that is, in such a way that the "center of gravity" of the two types is in a common location. This is the preferred manner, although other patterns of interleaving may be used.

Likewise, the preferred embodiments have equal numbers of sensing and calibration pixels, but the proportion of calibration pixels could be reduced while still benefiting from the underlying concept.

A typical method of operating the sensor is as follows:
1. Obtain image with no analyte/reagent present and no light produced: Idark(x,y);
2. Separate the image data into two images, pixel data Pdark(x,y) and calibration data "Cdark(x,y);
3. Add the analyte/reagent and obtain an image with light Ilight(x,y);
4. Separate this into two images, pixel data Plight(x,y) and calibration data Clight(x,y);
5. The uncompensated image is then calculated by Plight(x,y)−Pdark(x,y) (on a pixel basis);
6. The compensation signal is calculated from the calibration pixels as fnCal(Clight(x,y), Cdark(x,y)); and
7. Compute compensated image Output(x,y)={Plight(x,y)−Pdark(x,y)}×fnCal(x,y).

In the simplest case, fnCal could be linear, i.e., fnCal(x,y)=Cdark(x,y)/Clight(x,y). This is suitable where the error source changes linearly. However, the main use for this technique is to correct for temperature where the dark current rises exponentially with temperature. The calibration function can represent this, e.g., fnCal(x,y)=log(Cdark(x,y)/Clight(x,y)).

Depending on the design of the sense node, other errors may be significant and require a change to the calibration function. This can be computed arithmetically or determined empirically, and incorporated in a look-up table.

That which is claimed is:

1. A bio-optical sensor comprising:
a semiconductor substrate; and
an array of interlaced sensing pixels and calibration pixels on said semiconductor substrate for defining an image plane, said image plane receiving an analyte and a reagent that reacts with the analyte to produce light;
said sensing pixels generating signals as a function of the light produced by the reaction of the analyte and reagent, with said calibration pixels not being exposed to light.

2. A bio-optical sensor according to claim 1, wherein there is an equal number of said sensing pixels and said calibration pixels.

3. A bio-optical sensor according to claim 2, wherein said sensing pixels and said calibration pixels are alternately interlaced.

4. A bio-optical sensor according to claim 1, wherein said sensing pixels are arranged as a plurality of blocks of sensing pixels, and said calibration pixels are arranged as a plurality of blocks of calibration pixels, with each respective block comprising a plurality of pixels, and with said blocks of sensing pixels and said blocks of calibration pixels being interlaced.

5. A bio-optical sensor according to claim 4, wherein the signals generated by said sensing pixels at an edge of each block of sensing pixels are not used.

6. A bio-optical sensor according to claim 4, wherein each block of calibration pixels comprises between 20 to 30 calibration pixels; and wherein each block of sensing pixels comprises between 20 to 30 sensing pixels.

7. A bio-optical sensor according to claim 1, wherein the signals generated by said sensing pixels at an edge of said image plane are not used; and wherein signals generated by said calibration pixels at an edge of said image plane are also not used.

8. A bio-optical sensor according to claim 1, further comprising an opaque substance on said calibration pixels.

9. A bio-optical sensor according to claim 8, wherein said opaque substance comprises a metal layer.

10. A bio-optical sensor according to claim 1, wherein said image plane is divided so that the analyte and the reagent contact said sensing pixels but do not contact said calibration pixels.

11. A bio-optical sensor comprising:
a semiconductor substrate;
a plurality of blocks of sensing pixels on said semiconductor substrate and a plurality of blocks of calibration pixels on said semiconductor substrate, with said blocks of sensing pixels and said blocks of calibration pixels being interlaced, and with each block comprising M by N pixels with M and N being equal to or greater than 2;
said blocks of sensing pixels receiving an analyte and a reagent that reacts with the analyte to produce light, and said blocks of sensing pixels generating signals as a function of the light produced by the reaction of the analyte and reagent; and
an opaque layer on each calibration pixel for blocking the light produced.

12. A bio-optical sensor according to claim 11, wherein there is an equal number of said sensing pixels and said calibration pixels.

13. A bio-optical sensor according to claim 11, wherein said blocks of sensing pixels and said blocks of calibration pixels are alternately interlaced.

14. A bio-optical sensor according to claim 11, wherein the signals generated by said sensing pixels at an edge of each block of sensing pixels are not used.

15. A bio-optical sensor according to claim 11, wherein each block of calibration pixels comprises between 20 to 30 calibration pixels; and wherein each block of sensing pixels comprises between 20 to 30 sensing pixels.

16. A bio-optical sensor according to claim 11, wherein said blocks of sensing pixels and said blocks of calibration pixels define an image plane on said semiconductor substrate, and the signals generated by said sensing pixels at an edge of the image plane are not used, and signals generated by said calibration pixels at an edge of the image plane are also not used.

17. A bio-optical sensor according to claim 11, wherein said opaque layer comprises a metal layer.

18. A method for making a bio-optical sensor comprising:
forming an image plane on a substrate, the image plane comprising an array of interlaced sensing pixels and calibration pixels, the image plane for receiving an analyte and a reagent that reacts with the analyte to produce light; and
using the sensing pixels for generating signals as a function of the light produced by the reaction of the analyte and reagent, with the calibration pixels not being exposed to the light produced.

19. A method according to claim 18, wherein the substrate comprises a semiconductor substrate.

20. A method according to claim 18, wherein there is an equal number of sensing pixels and calibration pixels.

21. A method according to claim 20, wherein the sensing pixels and the calibration pixels are alternately interlaced.

22. A method according to claim 18, wherein the sensing pixels are arranged as a plurality of blocks of sensing pixels, and the calibration pixels are arranged as a plurality of blocks of calibration pixels, with each respective block comprising a plurality of pixels, and with the blocks of sensing pixels and the blocks of calibration pixels being interlaced.

23. A method according to claim 22, wherein the signals generated by the sensing pixels at an edge of each block of sensing pixels are not used.

24. A method according to claim 22, wherein each block of calibration pixels comprises between 20 to 30 calibration pixels; and wherein each block of sensing pixels comprises between 20 to 30 sensing pixels.

25. A method according to claim 18, wherein the signals generated by the sensing pixels at an edge of the image plane are not used; and wherein signals generated by the calibration pixels at an edge of the image plane are also not used.

26. A method according to claim 18, further comprising forming an opaque substance on the calibration pixels.

27. A method according to claim 26, wherein the opaque substance comprises a metal layer.

28. A method according to claim 18, wherein the image plane is divided so that the analyte and the reagent contact the sensing pixels but do not contact the calibration pixels.

* * * * *

UNITED STATES PATENT AND TRADEMARK OFFICE
CERTIFICATE OF CORRECTION

PATENT NO. : 7,447,385 B2 Page 1 of 1
APPLICATION NO. : 11/015242
DATED : November 4, 2008
INVENTOR(S) : Jeffrey Raynor It is certified that error appears in the above-identified patent and that said Letters Patent is hereby corrected as shown below:

Column 1, Line 5        Delete: "bi"
                        Insert: --bio--

Column 2, Line 33       Delete: "red"
                        Insert: --red,--

Column 3, Line 24       Delete: ""Cdark"
                        Insert: --Cdark--

Signed and Sealed this

Seventeenth Day of February, 2009

JOHN DOLL
*Acting Director of the United States Patent and Trademark Office*